United States Patent
Xie et al.

(10) Patent No.: US 12,156,738 B2
(45) Date of Patent: Dec. 3, 2024

(54) MULTIMODAL HUMAN-ROBOT INTERACTION SYSTEM FOR UPPER LIMB REHABILITATION

(71) Applicant: SOUTH CHINA UNIVERSITY OF TECHNOLOGY, Guangdong (CN)

(72) Inventors: Longhan Xie, Guangdong (CN); Siqi Cai, Guangdong (CN); Guofeng Li, Guangdong (CN); Shuangyuan Huang, Guangdong (CN)

(73) Assignee: SOUTH CHINA UNIVERSITY OF TECHNOLOGY, Guangdong (CN)

( * ) Notice: Subject to any disclaimer, the term of this patent is extended or adjusted under 35 U.S.C. 154(b) by 797 days.

(21) Appl. No.: 17/298,031

(22) PCT Filed: Oct. 31, 2019

(86) PCT No.: PCT/CN2019/114915
§ 371 (c)(1),
(2) Date: May 28, 2021

(87) PCT Pub. No.: WO2020/119319
PCT Pub. Date: Jun. 18, 2020

(65) Prior Publication Data
US 2022/0095989 A1     Mar. 31, 2022

(30) Foreign Application Priority Data
Dec. 15, 2018   (CN) .......................... 201811537912.7

(51) Int. Cl.
*A61B 5/389*     (2021.01)
*A61B 5/369*     (2021.01)
(Continued)

(52) U.S. Cl.
CPC .............. *A61B 5/389* (2021.01); *A61B 5/369* (2021.01); *A61H 1/0274* (2013.01); *A63B 23/12* (2013.01);
(Continued)

(58) Field of Classification Search
CPC ........ A61H 1/0274–0288; A61B 5/267; A61B 5/287
See application file for complete search history.

(56) References Cited

U.S. PATENT DOCUMENTS

| | | | |
|---|---|---|---|
| 6,454,679 B1 * | 9/2002 | Radow | A63B 22/0235 482/4 |
| 2004/0106881 A1 * | 6/2004 | McBean | A61B 5/389 601/5 |

(Continued)

FOREIGN PATENT DOCUMENTS

| | | |
|---|---|---|
| CN | 103750975 | 4/2014 |
| CN | 104173124 | 12/2014 |

(Continued)

OTHER PUBLICATIONS

"International Search Report (Form PCT/ISA/210) of PCT/CN2019/114915," mailed on Feb. 6, 2020, with English translation thereof, pp. 1-6.

*Primary Examiner* — Joseph D. Boecker
*Assistant Examiner* — Thomas W Greig
(74) *Attorney, Agent, or Firm* — JCIPRNET

(57) ABSTRACT

A multimodal human-robot interaction system for upper limb rehabilitation, including an electroencephalography signal acquisition and processing module, a robot module, a comprehensive affected upper limb muscle signal acquisition and processing module, a rehabilitation training evaluation module, and a virtual reality module. The electroencephalography signal acquisition and processing module captures a motion intention of a patient by means of elec- (Continued)

troencephalography signals to trigger rehabilitation training. The robot module assists an affected upper limb with rehabilitation exercise. The comprehensive affected upper limb muscle signal acquisition and processing module acquires and obtains a comprehensive assessment of the affected upper limb. The rehabilitation training evaluation module is used for processing and analyzing the comprehensive assessment of the affected upper limb, so as to obtain a quantitative evaluation of the affected upper limb during rehabilitation training. The virtual reality module is used for displaying a virtual environment for rehabilitation training, and interacting with the patient.

8 Claims, 1 Drawing Sheet

(51) Int. Cl.
*A61H 1/02* (2006.01)
*A63B 23/12* (2006.01)

(52) U.S. Cl.
CPC ............... *A61H 2201/1207* (2013.01); *A61H 2201/165* (2013.01); *A61H 2201/5015* (2013.01); *A61H 2230/105* (2013.01)

(56) References Cited

U.S. PATENT DOCUMENTS

| | | | | |
|---|---|---|---|---|
| 2006/0293617 | A1* | 12/2006 | Einav | A63B 23/03541 601/5 |
| 2007/0043308 | A1* | 2/2007 | Lee | A61H 1/0237 601/5 |
| 2011/0136626 | A1* | 6/2011 | Wei | A61B 5/224 482/6 |
| 2017/0181915 | A1* | 6/2017 | Ang | G06F 3/014 |
| 2019/0314680 | A1* | 10/2019 | Hwang | A63B 21/0023 |
| 2019/0384391 | A1* | 12/2019 | Li | G06F 3/011 |

FOREIGN PATENT DOCUMENTS

| | | |
|---|---|---|
| CN | 107157705 | 9/2017 |
| CN | 107320285 | 11/2017 |
| CN | 108261197 | 7/2018 |
| CN | 108304068 | 7/2018 |
| CN | 108814597 | 11/2018 |
| CN | 108888482 | 11/2018 |
| CN | 109568083 | 4/2019 |
| KR | 20180010781 | 1/2018 |
| WO | 2010040416 | 4/2010 |

\* cited by examiner

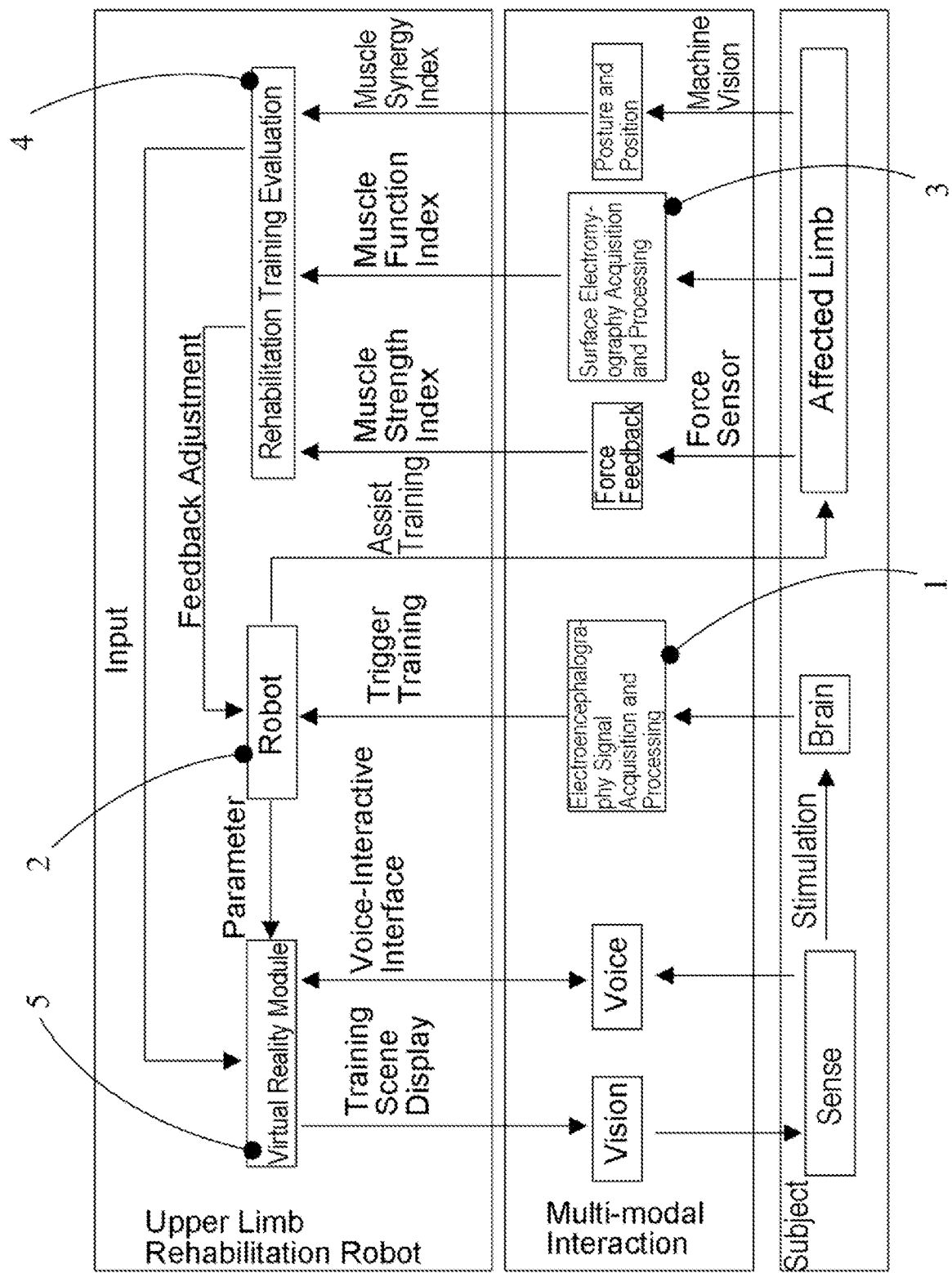

MULTIMODAL HUMAN-ROBOT INTERACTION SYSTEM FOR UPPER LIMB REHABILITATION

CROSS-REFERENCE TO RELATED APPLICATION

This application is a 371 of international application of PCT application serial no. PCT/CN2019/114915, filed on Oct. 31, 2019, which claims the priority benefit of China application no. 201811537912.7, filed on Dec. 15, 2018. The entirety of each of the above mentioned patent applications is hereby incorporated by reference herein and made a part of this specification.

TECHNICAL FIELD

The present invention relates to the field of upper limb rehabilitation, and more particularly to a multimodal human-robot interaction system for upper limb rehabilitation.

BACKGROUND

With the development of economy and the improvement of living standards, the population aging problem becomes increasingly prominent. Stroke affects thousands of people worldwide and nearly half of stroke survivors suffer from upper limb deficits making it difficult to perform activities of daily living. Physical therapy, which plays an important role in improving motor function, is a regular intervention for patients with stroke. However, conventional physical therapy mainly relied on therapists, which is labor-intensive and inefficient. Furthermore, many patients cannot receive a sufficient amount of rehabilitation training due to a lack of available therapists.

Furthermore, the existing rehabilitation training lacks the recording of objective data, does not have quantitative evaluation methods, and cannot provide effective feedback, thereby limit the final functional outcome of the affected upper limb. In addition, due to the repeated rehabilitation training movements, a patient often feels boring, and thus leads to a low interest in rehabilitation and even is unwilling to complete training.

Therefore, it is necessary to provide a novel upper limb rehabilitation robot training system, so as to achieve more effective and efficient upper limb rehabilitation, improve the interest of the entire training process, and increases the motivation and engagement of patients.

SUMMARY

The present invention discloses a multimodal human-robot interaction system for upper limb rehabilitation, including an electroencephalography signal acquisition and processing module, a robot module, a comprehensive affected upper limb muscle signal acquisition and processing module, a rehabilitation training evaluation module, and a virtual reality module. The multimodal human-robot interaction system for upper limb rehabilitation is controlled by electroencephalography signals. The electroencephalography signal acquisition and processing module captures features of electroencephalography signals to trigger rehabilitation training and fully reflects a rehabilitation motion intention of a patient. A muscle function state of an affected upper limb is reflected by acquiring and analyzing a surface electromyography signal in real time. A muscle strength index is reflected by force feedback data. A muscle synergy index is reflected by posture and position information of the patient captured by machine vision. A quantitative evaluation of the affected upper limb during rehabilitation training is obtained by calculating a total score of the three indexes. A rehabilitation training evaluation result, on one hand, is inputted into the robot as a rehabilitation training feedback parameter to adjust the training action, and on the other hand, is inputted into the virtual reality as a quantitative evaluation of the affected upper limb for intuitively displaying to the patient, so as to achieve safe, scientific, and interesting upper limb rehabilitation training. Furthermore, a virtual reality technology is utilized to improve the interest of the entire rehabilitation training process, and increases the motivation and engagement of patients.

In order to achieve the above objectives, the technical solution of the present invention is as follows.

A multimodal human-robot interaction system for upper limb rehabilitation, including an electroencephalography signal acquisition and processing module, a robot module, a comprehensive affected upper limb muscle signal acquisition and processing module, a rehabilitation training evaluation module, and a virtual reality module.

The electroencephalography signal acquisition and processing module is used for extracting a relevant feature parameter from an electroencephalography signal of a patient to obtain a motion intention of the patient, and then triggering a rehabilitation training action of the robot module.

The robot module performs the training action under the triggering of the electroencephalography signal acquisition and processing module and a quantitative evaluation parameter fed back by the rehabilitation training evaluation module, so as to help an affected upper limb of the patient to perform a spatial movement to complete a rehabilitation therapy.

The comprehensive affected upper limb muscle signal acquisition and processing module is used for acquiring and obtaining a comprehensive assessment of the affected upper limb.

The rehabilitation training evaluation module is used for processing and analyzing the comprehensive assessment of the affected upper limb, the comprehensive assessment includes a muscle function state index, a muscle strength index, and a muscle synergy index, respectively scoring the three indexes, and calculating a total score of the three indexes, so as to obtain a quantitative evaluation of the affected upper limb during a rehabilitation training.

The virtual reality module is used for displaying a virtual environment for the rehabilitation training, and increases motivation and engagement of the patient by providing feedback through multiple senses, wherein input parameters for the virtual reality module respectively come from the robot module and the rehabilitation training evaluation module.

Further, the muscle strength index is reflected by force feedback data. The muscle function index is reflected by feature parameters including an amplitude of a surface electromyography signal, an integrated electromyogram, a median frequency, and a mean frequency. The muscle synergy index is reflected by posture and position information of the patient captured by machine vision.

Further, respectively scoring the three indexes specifically includes the following steps.

Obtaining a score of the muscle function index by comparing feature values of surface electromyography signals of the patient and a healthy person, wherein the greater the difference between the two values is, the lower the score of the patient is. Obtaining a score of the muscle strength index through force feedback data, wherein the greater a value of the force is, the lower an active training degree of the patient is, and the lower the score of the patient is. Obtaining a score of the muscle synergy index by comparing motion data of the patient and a healthy person and calculating errors of a motion velocity and a track of the affected upper limb, wherein the greater the errors are, the lower the score of the patient is. Obtaining the quantitative evaluation result of the upper limb rehabilitation training of the patient by calculating the total score of the three indexes, wherein the score is proportional to the motion ability and rehabilitation training effect of the affected upper limb.

Further, the comprehensive affected upper limb muscle signal acquisition and processing module includes a surface electromyography acquisition and processing module, a force feedback apparatus, and a machine vision apparatus.

The surface electromyography acquisition and processing module obtains the muscle function state index of the affected upper limb by extracting a surface electromyography feature of an upper limb of the patient.

The force feedback apparatus obtains the muscle strength index of the affected upper limb by means of the acquired force feedback data.

The machine vision apparatus obtains the muscle synergy index of the affected upper limb by means of the captured posture and position data of the affected upper limb.

Further, the electroencephalography signal acquisition and processing module includes an electroencephalography signal acquisition portion, a multi-channel analog front-end amplification circuit portion, a multi-channel digital active circuit portion, and a multi-channel information processing portion. The electroencephalography signal acquisition portion acquires and transmits an electroencephalography signal of the patient to the multi-channel analog front-end circuit for amplification, and converts an analog quantity into a digital quantity so as to improve the anti-interference performance of the signal during transmission. The multi-channel digital active circuit portion caches and converts the digital signal, and then transmits the signal to the multi-channel information processing portion for storage and recovery. Finally the multi-channel information processing portion performs corresponding processes including feature extraction and pattern recognition, and outputs a signal to trigger the operation of the robot module.

Further, when the robot module is triggered by the signal outputted by the electroencephalography signal acquisition and processing module, the robot module is used for assisting the affected upper limb of the patient to perform passive rehabilitation training, active rehabilitation training, and active-passive rehabilitation training, and transmitting training data to the virtual reality module as an input.

Further, the surface electromyography signal acquisition and processing module includes a front-end amplification circuit portion, a notch filter portion, a filter portion, and a signal analysis portion. The front-end amplification circuit portion is used for amplifying the acquired surface electromyography signal. The notch filter portion is used for reducing the interference of a 50 Hz industrial frequency. The filter portion is used for filtering out low frequency and high frequency noises in the surface electromyography signal. The signal analysis portion is used for performing time domain analysis and frequency domain analysis on the surface electromyography signal, and extracting features including an amplitude, an integrated electromyography, a median frequency, and a mean frequency to reflect the muscle function state of the upper limb of the patient.

Further, the rehabilitation training evaluation module, on one hand, is inputted into the robot module as a rehabilitation training feedback parameter to adjust the training action, and on the other hand, is inputted into the virtual reality module as a quantitative evaluation of the affected upper limb for intuitively displaying to the patient.

Further, the virtual reality module comprises a training scene display portion and a voice-interactive interface portion; the inputs come from the robot module and the rehabilitation training evaluation module. The virtual reality module stimulates the patient by means of vision and voice, so as to increases the motivation and engagement of patients during rehabilitation training.

Compared with the prior art, the present invention has the following advantages and technical effects.

The present invention adopts electroencephalography control, fully reflects a rehabilitation intention of the patient, acquires the muscle function state of the affected upper limb in combination with surface electromyography signal feedback in real time, and provides comprehensive rehabilitation training evaluation in combination with force feedback and the posture and position information; furthermore, the present invention performs display interaction via the virtual reality module, forms a multimodal interaction-based upper limb rehabilitation robot training system, and achieves a safe, scientific, and interesting affected upper limb rehabilitation training process.

BRIEF DESCRIPTION OF THE DRAWINGS

FIG. 1 is a schematic view of a multimodal human-robot interaction system for upper limb rehabilitation.

In the figures: 1, electroencephalography signal acquisition and processing module; 2, robot module; 3, surface electromyography signal acquisition and processing module; 4, rehabilitation training evaluation module; and 5, virtual reality module.

DETAILED DESCRIPTION OF THE EMBODIMENTS

The invention will be further described hereafter with reference to specific embodiments, but is not limited to the specific embodiments.

As shown in FIG. 1, a multimodal human-robot interaction system for upper limb rehabilitation, including an electroencephalography signal acquisition and processing module 1, a robot module 2, a comprehensive affected upper limb muscle signal acquisition and processing module, a rehabilitation training evaluation module 4, and a virtual reality module 5.

The electroencephalography signal acquisition and processing module 1 is used for extracting a relevant feature parameter from an electroencephalography signal of a patient to obtain a motion intention of the patient, and then triggering a rehabilitation training action of the robot module 2.

The robot module 2 performs the training action under the triggering of the electroencephalography signal acquisition and processing module 1 and a quantitative evaluation parameter fed back by the rehabilitation training evaluation module 4, so as to help an affected upper limb of the patient to perform a spatial movement to complete a rehabilitation therapy.

The comprehensive affected upper limb muscle signal acquisition and processing module is used for acquiring and obtaining a comprehensive assessment of the affected upper limb. The muscle comprehensive assessment includes a muscle function state index, a muscle strength index, and a muscle synergy index. The affected upper limb muscle comprehensive data acquisition and processing module includes surface electromyography acquisition and processing module 3, a force feedback apparatus, and a machine vision apparatus.

The surface electromyography acquisition and processing module 3 obtains the muscle function state index of the affected upper limb by extracting a surface electromyography feature of an upper limb of the patient.

The force feedback apparatus obtains the muscle strength index of the affected upper limb by means of the acquired force feedback data.

The machine vision apparatus obtains the muscle synergy index of the affected upper limb by means of the captured posture and position data of the affected upper limb, compares the posture and position data with the motion data of a healthy person, analyzes and calculates the errors of the motion velocity and track of the affected upper limb.

The rehabilitation training evaluation module 4 is used for processing and analyzing the muscle function state index, the muscle strength index, and the muscle synergy index of the affected upper limb, and respectively scoring the three indexes which respectively includes the following steps: obtaining the score of the muscle function index by comparing feature values of surface electromyography signals of the patient and a healthy person, wherein the greater the difference between the two values is, the lower the score of the patient is; obtaining the score of the muscle strength index through force feedback data, wherein the greater the value of force is, the lower the active training degree of the patient is, and the lower the score of the patient is; obtaining the score of the muscle synergy index by comparing motion data of the patient and a healthy person and calculating errors of a motion velocity and a track of the affected upper limb, wherein the greater the errors are, the lower the score of the patient is; and obtaining the quantitative evaluation result of the upper limb rehabilitation training of the patient by calculating the total score of the three indexes, wherein the score reflects the motion ability and rehabilitation training effect of the affected upper limb, that is, the higher the score is, the better the motion ability and rehabilitation training effect of the affected upper limb are.

The virtual reality module 5 is used for displaying a virtual environment for upper limb rehabilitation training, and stimulating the patient by means of vision and voice, wherein the input for the virtual reality module respectively come from the robot module 2 and the rehabilitation training evaluation module 4.

The electroencephalography signal acquisition and processing module 1 includes an electroencephalography signal acquisition portion, a multi-channel analog front-end amplification circuit portion, a multi-channel digital active circuit portion, and a multi-channel information processing portion, wherein the electroencephalography signal acquisition portion acquires and transmits an electroencephalography signal of the patient to the multi-channel analog front-end circuit for amplification, and converts an analog quantity into a digital quantity so as to improve the anti-interference performance of the signal during transmission; the multi-channel digital active circuit portion caches and converts the digital signal, and then transmits the signal to the multi-channel information processing portion for storage and recovery; and finally the multi-channel information processing portion performs corresponding processes including feature extraction and pattern recognition, and outputs an signal to trigger the operation of the robot module 2.

The electroencephalography signal acquisition and processing module 1 captures a motion intention of the patient by acquiring an electroencephalography signal, analyzing and extracting a relevant feature from the electroencephalography signal of the patient, then transmits the motion intention to the robot module 2, and triggers a rehabilitation training movement, so as to fully reflect a subjective intention of the patient.

The robot module 2 is connected to the upper limb of the patient; when the robot module is triggered by the output of the electroencephalography signal acquisition and processing module 1, the robot module assists the patient to complete a rehabilitation training movement, can provide targeted training modes for patients at different rehabilitation stages, drives the affected upper limb of the patient to perform passive rehabilitation training, active rehabilitation training, and active-passive rehabilitation training, and transmitting training data to the virtual reality module 5 as the input.

The surface electromyography signal acquisition and processing module 3 includes a front-end amplification circuit portion, a notch filter portion, a filter portion, and a signal analysis portion, wherein the front-end amplification circuit portion is used for amplifying the acquired surface electromyography signal; the notch filter is used for reducing the interference of a 50 Hz industrial frequency; the filter portion is used for filtering out low frequency and high frequency noises in the surface electromyography signal; and the signal analysis portion is used for performing time domain analysis and frequency domain analysis on the surface electromyography signal, and extracting features comprising an amplitude, an integrated electromyography, a median frequency, and a mean frequency to reflect the muscle function state of the upper limb of the patient, and transmitting an analysis result to the rehabilitation training evaluation module 4.

The rehabilitation training evaluation module 4 analyzes and processes the muscle strength index, the muscle function index, and the muscle synergy index, wherein the surface electromyography acquisition and processing module (3) obtains the muscle function state index of the affected upper limb by extracting a surface electromyography feature of the upper limb of the patient; the force feedback apparatus obtains the muscle strength index of the affected upper limb by means of the acquired force feedback data; and the machine vision apparatus obtains the muscle synergy index of the affected upper limb by means of the captured posture and position data of the affected upper limb. The three indexes are respectively scored, and a total score is calculated as a quantitative evaluation of the affected upper limb during rehabilitation training. The evaluation data, on one hand, is inputted into the robot module 2 as a rehabilitation training feedback parameter to adjust the training action, so as to achieve effective and efficient rehabilitation training, and on the other hand, is inputted into the virtual reality module 5 as a quantitative evaluation of the affected upper limb for intuitively displaying to the patient, so as to increases motivation and engagement of the patient during rehabilitation training.

The virtual reality module 5 includes a training scene display portion and a voice-interactive interface portion. The inputs come from the robot module 2 and the rehabilitation training evaluation module 4. The virtual reality module stimulates the patient by means of vision and voice, so as to increases the motivation and engagement of patients during rehabilitation training. The virtual reality module 5 is used for displaying a virtual environment for rehabilitation training, and interacting with the patient by means of voice-interactive interface and multi-level stimulation for senses, so as to realize the interaction between the system and patients, and enhance the interest of rehabilitation training.

The present invention forms the multimodal human-robot interaction system for upper limb rehabilitation through the electroencephalography signal acquisition and processing module, the robot module, the electroencephalography signal acquisition and processing module, the rehabilitation training evaluation module and the virtual reality module, which achieves a safe, scientific, and interesting upper limb rehabilitation training.

A use process of the present embodiment is as follows.

In a practical embodiment, after the electroencephalography signal acquisition and processing module 1 starts to operate, the electroencephalography signal acquisition portion acquires and transmits an electroencephalography signal of the patient to the multi-channel analog front-end circuit for amplification, and converts an analog quantity into a digital quantity so as to improve the anti-interference performance of the signal during transmission. The multi-channel digital active circuit portion caches and converts the digital signal, and then transmits the signal to the multi-channel information processing portion for storage and recovery; and finally the multi-channel information processing portion performs corresponding processes including feature extraction and pattern recognition, and outputs an signal to trigger the operation of the robot module 2. An end of the robot module 2 is connected to an upper limb of the patient; the robot module drives the upper limb of the patient to perform passive rehabilitation training, active rehabilitation training, or active-passive rehabilitation training, and transmitting training data to the virtual reality module 5 as an input. In the process that the robot module 2 assists the affected upper limb to perform rehabilitation training, the surface electromyography signal acquisition and processing module 3 acquires a surface electromyography signal of the affected upper limb in real time, analyzes the surface electromyography signal to obtain the muscle function index, and transmits the muscle function index to the rehabilitation training evaluation module 4. Furthermore, the force feedback apparatus acquires acting force data between the affected upper limb and the robot module 2, and analyzes the acting force data to obtain the muscle strength index; the machine vision apparatus captures the posture and position data of the affected upper limb, and analyzes the posture and position data to obtain the muscle synergy index; and the three indexes are processed and analyzed by the rehabilitation training evaluation module 4, so as to obtain a quantitative evaluation of the affected upper limb during rehabilitation training. The quantitative evaluation output, on one hand, is inputted into the robot module 2 as a rehabilitation training feedback parameter to adjust the training action, so as to achieve effective and efficient rehabilitation training, and on the other hand, is inputted into the virtual reality module 5 as a quantitative evaluation of the affected upper limb for intuitively displaying to the patient. The virtual reality module 5 displays a virtual motion scene for the upper limb of the patient, thereby improving the interest of the entire training process. Furthermore, the virtual reality module performs voice interaction with the patient, so as to stimulate the motivation of the patient.

According to the above disclosure and teaching of the specification, a person skilled in the art can vary and modify the above embodiments. Therefore, the present invention is not limited to the specific embodiments disclosed and described above, and the modifications and variations made to the present invention should also fall into the protection scope of the claims of the present invention. According to the above disclosure and teaching of the specification, a person skilled in the art can vary and modify the above embodiments. Therefore, the present invention is not limited to the specific embodiments disclosed and described above, and the modifications and variations made to the present invention should also fall into the protection scope of the claims of the present invention.

What is claimed is:

1. A multimodal human-robot interaction system for upper limb rehabilitation, comprising an electroencephalography signal acquisition and processing module, a robot module, a comprehensive affected upper limb muscle signal acquisition and processing module, a rehabilitation training evaluation module, and a virtual reality module, wherein the electroencephalography signal acquisition and processing module is used for extracting a relevant feature parameter from an electroencephalography signal of a patient to obtain a motion intention of the patient, and then triggering a rehabilitation training action of the robot module;

the robot module performs the training action under the triggering of the electroencephalography signal acquisition and processing module and a quantitative evaluation parameter fed back by the rehabilitation training evaluation module, so as to help an affected upper limb of the patient perform a spatial movement to complete a rehabilitation therapy;

the comprehensive affected upper limb muscle signal acquisition and processing module is used for acquiring and obtaining a comprehensive assessment of the affected upper limb;

the rehabilitation training evaluation module is used for processing and analyzing the comprehensive assessment of the affected upper limb, wherein the comprehensive assessment comprises a muscle function state index, a muscle strength index, and a muscle synergy index, respectively scoring the three indexes, and calculating a total score of the three indexes, so as to obtain a quantitative evaluation of the affected upper limb during rehabilitation training; and the virtual reality module is used for displaying a virtual environment for rehabilitation training, and increases motivation and engagement of the patient by providing feedback through multiple senses, wherein input parameters for the virtual reality module respectively come from the robot module and the rehabilitation training evaluation module, wherein the muscle strength index is reflected by force feedback data; the muscle function state index is reflected by feature parameters comprising an amplitude of a surface electromyography signal, an integrated electromyogram, a median frequency, and a mean frequency; and the muscle synergy index is reflected by posture and position information of the patient captured by machine vision, wherein respectively scoring the three indexes specifically comprise the following steps:

obtaining the score of the muscle function state index by comparing feature values of surface electromyography signals of the patient and a healthy person, wherein the greater the difference between the two values is, the lower the score of the patient is;

obtaining the score of the muscle strength index through force feedback data, wherein the greater the value of force is, the lower the active training degree of the patient is, and the lower the score of the patient is;

obtaining the score of the muscle synergy index by comparing motion data of the patient and a healthy person and calculating errors of a motion velocity and a track of the affected upper limb, wherein the greater the errors are, the lower the score of the patient is; and obtaining the quantitative evaluation result of the upper limb rehabilitation training of the patient by calculating the total score of the three indexes, wherein the score is proportional to the motion ability and rehabilitation training effect of the affected upper limb.

2. The multimodal human-robot interaction system for upper limb rehabilitation according to claim 1, wherein the comprehensive affected upper limb muscle signal acquisition and processing module comprises a surface electromyography acquisition and processing module, a force feedback apparatus, and a machine vision apparatus, wherein the surface electromyography acquisition and processing module obtains the muscle function state index of the affected upper limb by extracting a surface electromyography feature of an upper limb of the patient;

the force feedback apparatus obtains the muscle strength index of the affected upper limb by means of the acquired force feedback data; and the machine vision apparatus obtains the muscle synergy index of the affected upper limb by means of the captured posture and position data of the affected upper limb.

3. The multimodal human-robot interaction system for upper limb rehabilitation according to claim 2, wherein specifically, the machine vision apparatus obtains the muscle synergy index of the affected upper limb by capturing the posture and position data of the affected upper limb, comparing the posture and position data with the motion data of a healthy person, and analyzing and calculating the errors of the motion velocity and track of the affected upper limb.

4. The multimodal human-robot interaction system for upper limb rehabilitation according to claim 1, wherein the electroencephalography signal acquisition and processing module comprises an electroencephalography signal acquisition portion, a multi-channel analog front-end amplification circuit portion, a multi-channel digital active circuit portion, and a multi-channel information processing portion, wherein the electroencephalography signal acquisition portion acquires and transmits an electroencephalography signal of the patient to the multi-channel analog front-end circuit for amplification, and converts an analog quantity into a digital quantity so as to improve the anti-interference performance of the signal during transmission; the multi-channel digital active circuit portion caches and converts the digital signal, and then transmits the signal to the multi-channel information processing portion for storage and recovery; and finally the multi-channel information processing portion performs corresponding processes including feature extraction and pattern recognition, and outputs an signal to trigger the operation of the robot module.

5. The multimodal human-robot interaction system for upper limb rehabilitation according to claim 1, wherein when the robot module is triggered by the signal outputted by the electroencephalography signal acquisition and processing module, the robot module is used for assisting the affected upper limb of the patient to perform passive rehabilitation training, active rehabilitation training, and active-passive rehabilitation training, and transmitting training data to the virtual reality module as an input.

6. The multimodal human-robot interaction system for upper limb rehabilitation according to claim 1, wherein the surface electromyography acquisition and processing module comprises a front-end amplification circuit portion, a notch filter portion, a filter portion, and a signal analysis portion, wherein the front-end amplification circuit portion is used for amplifying the acquired surface electromyography signal; the notch filter portion is used for reducing the interference of a 50 Hz industrial frequency; the filter portion is used for filtering out low frequency and high frequency noises in the surface electromyography signal; and the signal analysis portion is used for performing time domain analysis and frequency domain analysis on the surface electromyography signal, and extracting features comprising the amplitude of the surface electromyography signal, the integrated electromyography, the median frequency, and the mean frequency to reflect the muscle function state index of the affected upper limb of the patient.

7. The multimodal human-robot interaction system for upper limb rehabilitation according to claim 1, wherein the output data of the rehabilitation training evaluation module, on one hand, is inputted into the robot module as a rehabilitation training feedback parameter to adjust the training action, and on the other hand, is inputted into the virtual reality module as a quantitative evaluation of the affected upper limb for intuitively displaying to the patient.

8. The multimodal human-robot interaction system for upper limb rehabilitation according to claim 1, wherein the virtual reality module comprises a training scene display portion and a voice-interactive interface portion; the inputs come from the robot module and the rehabilitation training evaluation module; the virtual reality module stimulates the patient by means of vision and voice, so as to increases the motivation and engagement of patients during rehabilitation training.

* * * * *